(12) United States Patent
Ikeda et al.

(10) Patent No.: US 8,920,839 B2
(45) Date of Patent: Dec. 30, 2014

(54) DRY-COATED ORALLY-DISINTEGRATING TABLET

(75) Inventors: Yuki Ikeda, Ibaraki (JP); Yasushi Ochiai, Ibaraki (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 11 days.

(21) Appl. No.: 13/320,819

(22) PCT Filed: May 19, 2010

(86) PCT No.: PCT/JP2010/058429
§ 371 (c)(1), (2), (4) Date: Nov. 16, 2011

(87) PCT Pub. No.: WO2010/134540
PCT Pub. Date: Nov. 25, 2010

(65) Prior Publication Data
US 2012/0064162 A1    Mar. 15, 2012

(30) Foreign Application Priority Data
May 20, 2009    (JP) ................................. 2009-122476

(51) Int. Cl.
| A61K 9/36 | (2006.01) |
| A61K 9/00 | (2006.01) |
| A61K 9/28 | (2006.01) |
| A61K 31/167 | (2006.01) |
| A61K 31/426 | (2006.01) |

(52) U.S. Cl.
CPC .............. *A61K 9/0056* (2013.01); *A61K 9/2813* (2013.01); *A61K 9/284* (2013.01); *A61K 9/286* (2013.01); *A61K 9/2866* (2013.01); *A61K 31/167* (2013.01); *A61K 31/426* (2013.01); *A61K 9/2893* (2013.01)
USPC ....................................................... 424/480

(58) Field of Classification Search
None
See application file for complete search history.

(56) References Cited

U.S. PATENT DOCUMENTS

| 6,596,311 | B1 | 7/2003 | Dobetti |
| 2003/0124184 | A1 | 7/2003 | Mezaache et al. |
| 2004/0113319 | A1* | 6/2004 | Kondo et al. ................. 264/319 |
| 2005/0106240 | A1 | 5/2005 | Tanaka et al. |
| 2005/0202082 | A1 | 9/2005 | Hibino et al. |
| 2007/0275058 | A1 | 11/2007 | Tanaka et al. |
| 2008/0274178 | A1 | 11/2008 | Imamoto et al. |
| 2008/0317851 | A1* | 12/2008 | Appel et al. .................. 424/465 |
| 2009/0208576 | A1 | 8/2009 | Gandhi et al. |

FOREIGN PATENT DOCUMENTS

| CA | 2 599 617 | 9/2006 |
| JP | 11-035451 | 2/1999 |
| JP | 2001-278812 | 10/2001 |
| JP | 2002-505269 | 2/2002 |
| JP | 2005-139168 | 6/2005 |
| JP | 2008-044870 | 2/2008 |
| WO | 98/02185 | 1/1998 |
| WO | 01/98067 | 12/2001 |
| WO | 03/028706 | 4/2003 |
| WO | 2005/037254 | 4/2005 |
| WO | WO 2005/097041 | * 10/2005 |
| WO | 2005/123040 | 12/2005 |
| WO | 2006/092207 | 9/2006 |
| WO | 2007/018192 | 2/2007 |
| WO | 2007/113856 | 10/2007 |
| WO | 2009/054432 | 4/2009 |

OTHER PUBLICATIONS

English translation of the International Preliminary Report on Patentability, 2011.
International Search Report issued Aug. 17, 2010 in International (PCT) Application No. PCT/JP2010/058429.
Yuichi Ozeki, "One-Step Dry Coated Tablets (OSDRC®): Process Development and Study of their physical Characteristics", J. Jpn. Soc. Pharm. Mach. & Eng., vol. 14, No. 4, 2005, pp. 12-21 (with partial English translation).
Chinese Office Action, with English translation, issued Dec. 5, 2012 in counterpart Chinese Patent Application No. 201080032989.4.
Chinese Search Report, with English translation, issued Nov. 27, 2012 in counterpart Chinese Patent Application No. 201080032989.4.
Extended European Search Report issued Aug. 27, 2013 in corresponding European Patent Application No. 10777773.2.

* cited by examiner

*Primary Examiner* — Ileana Popa
*Assistant Examiner* — Alissa Prosser
(74) *Attorney, Agent, or Firm* — Wenderoth, Lind & Ponack, L.L.P.

(57) ABSTRACT

The purpose of the present invention is to provide a press-coated orally-disintegrating tablet characterized by containing an inner core which has an excellent disintegratability in oral cavity and a suitable hardness as a whole tablet. The present invention relates to a press-coated orally-disintegrating tablet with an outer layer surrounding an inner core wherein the inner core has a thickness in the range of 10 to 90% per that of the whole tablet, and the outer layer comprises (a) microcrystalline cellulose, (b) an inorganic excipient, and (c) one or more particular ingredients selected from the group consisting of crospovidone, starches, low substituted hydroxypropylcellulose and carmellose.

6 Claims, No Drawings

DRY-COATED ORALLY-DISINTEGRATING TABLET

This application is a U.S. national stage of International Application No. PCT/JP2010/058429 filed May 19, 2010.

TECHNICAL FIELD

The invention relates to a press-coated formulation (hereafter, also referred as a press-coated orally-disintegrating tablet) wherein its inner core is a powder/granular material with poor formability; its outer layer surrounds the inner core; and its pressed tablet has a suitable hardness and an excellent disintegratability in oral cavity.

In detail, the invention relates to a press-coated orally-disintegrating tablet characterized in that its outer layer rapidly disintegrates even when the tablet is taken with a small amount of water or without water, and then granules or powders in its inner cores are dispersed in oral cavity.

BACKGROUND ART

To the arrival of the aging society, the development of orally-disintegrating tablets which can be easily taken by the elderly who have hardness or difficulty in swallowing tablets has been ongoing. With this development, requests for developing orally-disintegrating tablets containing various active ingredients are growing. In case that an active ingredient has a bitter taste, the masking of the bitter taste will be necessary for formulating it into orally-disintegrating tablets and the like. Also, controlled release of an active ingredient may be necessary for increasing the bioavailability of the active ingredient. However, many of the above-mentioned functional particles tend to give some adverse affects to the formulation of tablets (for example, they lack sufficient hardness when homogenously distributed in a tablet), thus it is necessary to add a large amount of additives such as an excipient and a binder to avoid the adverse affects, which make the tablet in an inconvenient big size.

Patent Reference 1 discloses a press-coated rapidly disintegrating tablet as a unique form which has not been well known before. A press-coated tablet has a double-layered structure consisting of the inner core and the outer layer and attracts attentions as a novel technique of formulating tablets. However, the press-coated formulations disclosed in Patent Reference 1 were designed focused on the solubility and degradability of the inner core, and the ingredients of both the inner core and the outer layer comprise ingredients with formability (for example, it appears that the ingredients of the inner core in Patent Reference 1 has formability and a certain hardness, as figured out in the results of Example 2 in which only the ingredients of the inner core were compressed into tablets). Thus, approaches to the application using powder/granular materials with poor formability were not tried, hence Patent Reference 1 disclosed only a limited range of the ingredients of the inner core. Also, the outer layer of the press-coated tablet disclosed in Patent Reference 1 mainly comprises erythritol as a sugar alcohol, and the combination of the essential ingredients of the outer layer of the present invention were not disclosed.

Patent Reference 2 discloses trials applying microcapsule-like granules to the ingredients of the inner core in relation to the formulation in Patent Reference 1 described above. That is, Patent Reference 2 discloses the study to apply microcapsule-like granules to the inner core of the press-coated tablet, and some successful examples of press-coated formulations containing microcapsule-like granules in their inner cores which were prepared using the outer layers comprising lactose and microcrystalline cellulose according to a certain method. However, Patent Reference 2 discloses only the invention of the press-coated tablet containing microcapsule-like granules in its inner core, it does not disclose or suggest any study to apply the press-coated tablets to orally-disintegrating tablets. Additionally, in Patent Reference 2, there was no study about applicable ingredients for the outer layer in the press-coated formulation containing microcapsule-like granules in their inner cores, other than lactose and microcrystalline cellulose. Of course, Patent Reference 2 does not disclose the combination of the essential ingredients of the outer layers of the present invention.

The orally-disintegrating tablet in Patent Reference 3 is characterized in that comprises an active ingredient, microcrystalline cellulose and an inorganic excipient without any disintegrant. Also, as described therein, the orally-disintegrating tablet of Patent Reference 3 has a higher hardness shortly after the compression and more excellent degradability compared with those of orally-disintegrating tablets comprising crospovidone and low substituted hydroxypropylcellulose (for example, Example 5 and comparative Example 5-9). Also, Patent Reference 3 describes that "the present invention without any disintegrant holds a predominant position because disintegrants have side effects that lower the quality of tablets by decreasing the hardness of the tablets, inducing a roughness on the surface of the tablets due to their moisture absorption, and worsening the feeling of the tablets in oral cavity with oral dryness due to their absorption of saliva". Patent Reference 3 also lacks a disclosure and suggestion related to the press-coated formulations disclosed in the above Patent References 1 and 2.

Patent Reference 4 discloses an orally-disintegrating tablet comprising an inorganic excipient but does not describe a specific disclosure relating to a press-coated formulation.

[Patent Reference 1] WO2003/028706
[Patent Reference 2] WO2005/097041
[Patent Reference 3] WO2005/123040
[Patent Reference 4] WO2007/018192

DISCLOSURE OF INVENTION

Problem to be Solved by the Invention

As described above, in order to develop orally-disintegrating tablets, it is general to use various functional ingredients/particles in tablets. However, when the used functional ingredients/particles have adverse affects on the formability of the tablets, it is necessary to do some improvement because additional additives are necessary to minimize the adverse affects and thereby the tablets are enlarged.

On the other hand, the press-coated tablets disclosed in Patent References 1 and 2 are interesting as a novel technique for tablets, and in particular, Patent Reference 2 discloses examples of preparations containing microcapsule-like granules in the inner core, hence it would be expected to apply the formulation to some functional formulations such as orally-disintegrating tablets. However, press-coated tablets with the outer layer similar to that of the formulation disclosed in Patent Reference 2 had a remarkably poor oral disintegratability (see, Comparative Examples 1 to 3 of the present invention). We also found that the sufficient hardness were not achieved when press-coated tablets containing particles without formability were prepared using the outer layers disclosed in Patent Reference 1 which is directed to a pressed-coated tablet undergoing quick disintegration (see, Comparative Examples 1 to 4 of the present invention).

As described above, in order to prepare a press-coated tablet with double-layered structure consisting an inner core and an outer layer, in particular, a tablet containing particle without formability in its inner core, it is necessary to maintain the hardness of the tablet only with its outer layer, thus the outer layer of the tablet is required to be harder than a normal tablet. On the other hand, in order to prepare an orally-disintegrating tablet, it is necessary to reduce the hardness thereof to obtain a rapid degradability thereof. Thus, it has been difficult to maintain such strong harness for a press-coated tablet having the orally-disintegrating property.

The purpose of the present invention is to newly develop a press-coated formulation characterized in that its inner core comprises powder/granular material with poor formability and provide a press-coated orally-disintegrating tablet with an excellent disintegratability and a suitable hardness as a whole tablet.

Means to Solve the Problem

In general, it is difficult to let a tablet contain a large amount of particles having poor formability (e.g. functional particles) or a powder of active ingredient, thus the present inventors tried to prepare a tablet in which its inner core comprises such particles or such powders and its outer layer surrounds the inner core. In preparing such press-coated tablet comprising a powder/granular material with poor formability as mentioned above, it was extremely difficult to achieve a suitable hardness as a whole tablet while maintaining an oral disintegratability. However, the present inventors have extensively studied and then have found that the above problem can be solved by using a combination of particular ingredients in the outer layer. That is, the present inventors have found that it is possible to prepare a press-coated orally-disintegrating tablet with an outer layer surrounding its inner core wherein the inner core comprises a powder/granular material with poor formability; the outer layer comprises microcrystalline cellulose, an inorganic excipient and particular ingredients described below; and the pressed tablet has a suitable hardness and disintegratability as a whole tablet. In more detail, the present invention provides a press-coated orally-disintegrating tablet wherein the inner core has a thickness in the range of 10 to 90% of that of the whole tablet, and the outer layer comprises (a) microcrystalline cellulose, (b) an inorganic excipient, and (c) one or more particular ingredients selected from the group consisting of crospovidone, starches, low substituted hydroxypropylcellulose and carmellose, and the pressed tablet has a sufficient hardness and an excellent disintegratability in a oral cavity even when the inner core has poor formability.

The present invention provides inventions of various embodiments described below.

Term 1

A press-coated orally-disintegrating tablet with an outer layer surrounding an inner core wherein the inner core has a thickness in the range of 10 to 90% per that of the whole tablet, and the outer layer comprises (a) microcrystalline cellulose, (b) an inorganic excipient, and (c) one or more particular ingredients selected from the group consisting of crospovidone, starches, low substituted hydroxypropylcellulose and carmellose.

Term 2

The press-coated orally-disintegrating tablet of Term 1 wherein the inner core is a powder/granular material with poor formability.

Term 3

The press-coated orally-disintegrating tablet of Term 1 or 2 wherein the microcrystalline cellulose (a) is contained in the range of 5 to 80 wt % per 100 wt % of the outer layer.

Term 4

The press-coated orally-disintegrating tablet of any one of Terms 1 to 3 wherein the inorganic excipient (b) is contained in the range of 10 to 80 wt % per 100 wt % of the outer layer.

Term 5

The press-coated orally-disintegrating tablet of any one of Terms 1 to 4 wherein the total content of the particular ingredient (s) (c) is in the range of 1 to 40 wt % per 100 wt % of the outer layer.

Term 6

The press-coated orally-disintegrating tablet of any one of Terms 1 to 5 wherein the particular ingredient(s) (c) are one or more selected from the group consisting of crospovidone, starches and low substituted hydroxypropylcellulose.

Term 7

The press-coated orally-disintegrating tablet of any one of Terms 1 to 6 wherein the starches are corn starch.

Term 8

The press-coated orally-disintegrating tablet of any one of Terms 1 to 7 wherein the inner core has a thickness in the range of 20 to 80% of that of the whole tablet.

Term 9

The press-coated orally-disintegrating tablet of any one of Terms 1 to 8 wherein the porosity in the outer layer is 1 to 40%.

Term 10

The press-coated orally-disintegrating tablet of any one of Terms 1 to 9 wherein the inner core comprises an active ingredient.

Term 11

The press-coated orally-disintegrating tablet of any one of Terms 1 to 10 wherein the microcrystalline cellulose (a) is contained in the range of 10 to 70 wt % per 100 wt % of the outer layer.

Term 12

The press-coated orally-disintegrating tablet of any one of Terms 1 to 11 wherein the inner core comprises a powder, a granulated material or a powder/granular material which has poor formability, except for a microcapsule-like functional particle.

Effect of the Invention

The present invention can provide a press-coated orally-disintegrating tablet comprising a large amount of a powder/granular material with poor formability in its inner core, which has an excellent disintegratability and a suitable hardness as a whole tablet.

BEST MODE FOR CARRYING OUT THE INVENTION

The press-coated orally-disintegrating tablet of the present invention composes of an "inner core" which comprises a powder/granular material with poor formability such as a microcapsule-like functional particle and an "outer layer" which surrounds the inner core to give suitable hardness and disintegratability to the formed tablet. Also, the present invention can be applied to a powder, a granulated material or a powder/granular material with poor formability besides a microcapsule-like functional particle in its inner core to provide a tablet having sufficient hardness and disintegratability.

In the present invention, the "outer layer" comprises (a) microcrystalline cellulose, (b) an inorganic excipient and (c) one or more particular ingredients selected from the group consisting of crospovidone, starches, low substituted hydroxy-propylcellulose and carmellose. Using the combination of these ingredients, it becomes possible to prepare a press-coated orally-disintegrating tablet with sufficient hardness and excellent disintegratability even when an inner core therein has poor formability.

The term "orally-disintegrating tablet" means a tablet which rapidly disintegrates in oral cavity without water. In detail, it means a tablet in which its inner core and outer layer disintegrate or disperse within 60 sec, preferably within 45 sec, or even more preferably within 30 sec on an actual disintegration test in a human oral cavity or in a device. A device for the disintegration test includes, for example, ODT-101 (manufactured by Toyama Sangyo Co., Ltd.). In the actual disintegration test in a human oral cavity, the time from putting a tablet into the oral cavity to the complete oral disintegration was measured as the oral disintegration time. After the tests, the recipients took out the test sample from their oral cavity and washed their oral cavity with clean water.

The tablet hardness of the present invention was given by measuring the force required for diametrically crushing the tablet using a tablet hardness tester (PORTABLE CHECKER PC-30, manufactured by Okada Seiko Co., Ltd.). The "absolute hardness" was calculated using the obtained tablet hardness according to the following formula. The "absolute hardness" is a value obtained by dividing the hardness measured with the tablet hardness tester by the longitudinal sectional area (tablet diameter (mm)×tablet thickness (mm)).

The absolute hardness($N/mm^2$)=the hardness($N$)/the longitudinal sectional area($mm^2$).

In the present invention, the term "with suitable hardness and disintegratability" used herein means that the balance of the absolute hardness and the orally-disintegrating time is good. The term "HDBI" used herein is an abbreviation of Hardness and Disintegrating Balance Index, and calculated as an index of the balance of the absolute hardness and the orally-disintegrating time according to the following formula. The larger value means the more excellent balance of the hardness and the disintegratability. In detail, the orally-disintegrating tablet of the present invention has the HDBI value of 0.15 or more, preferably 0.2 or more, more preferably 0.25 or more, and even more preferably 0.3 or more.

HDBI($N/mm^2 \cdot sec$)=the absolute hardness($N/mm^2$)/the orally-disintegrating time(sec)

In the present invention, "a wide acceptable range of compressive force" means that the range of the compressive force is wide in the tableting process in preparing the orally-disintegrating tablet with suitable hardness and disintegratability, i.e., little change in the hardness and disintegratability can be induced at various compressive forces. If the range of the compressive force is narrow in preparing an orally-disintegrating tablet, it may be necessary to modify the compressive force for each tablet, or re-modify the compressive force during the tableting process. Additionally, there is a worry that the product can fail to achieve a good balance of the hardness and the disintegratability. Considering the industrial production of the tablet, therefore, it is important to design a formula with a wide acceptable compressive force, i.e., the hardness and the disintegratability are little changed even when the compressive force is varied.

In the press-coated orally-disintegrating tablet containing a poor formable inner core, the hardness and disintegratability thereof depends on only the formula of the outer layer, thus it difficult to achieve a good balance of the hardness and the disintegratability compared with a unilayered orally-disintegrating tablet (general orally-disintegrating tablet) or a press-coated orally-disintegrating tablet containing a formable inner core. Even if a good balance between the hardness and the disintegratability was achieved, it was quite difficult to control the compressive force in a wide acceptable range.

Generally, the porosity can be calculated according to the following formula:

The porosity of the tablet(%)=(1−Wt/(ρ×$V$))×100

ρ: the true density of the tablet ($mg/mm^3$),
V: the volume of the tablet ($mm^3$),
Wt: the weight of the tablet (mg).

In the present invention, the porosity of the outer layer can be calculated according to the following formula:

The porosity of the outer layer(%)=(1−Wt/(ρ×3.14× $D^2$×T))×100

ρ: the true density of the outer layer ($mg/mm^3$),
D: the radius of the outer layer (under-portion) (mm),
T: the thickness of the outer layer (under-portion) (mm),
Wt: the weight of the outer layer (under-portion) (mg).

In the present invention, the thickness of the inner core was calculated as described below. The thickness of the whole tablet was measured by a digital caliper (manufactured by Mitutoyo Co., Ltd.). The press-coated tablet was diametrically divided, the cross sectional surface was analyzed using a digital microscope (VHX-500, manufactured by Keyence Co., Ltd.), and the thicknesses of the upper portion and the under portion of the outer layer were measured.

The thickness of the inner core(mm)=the thickness of the whole tablet(mm)−the sum(mm) of thicknesses of the upper and under portion in the outer layer In the present invention, the term "ratio of the thickness of the inner core" means a ratio of the thickness of the inner core per the thickness of the whole tablet, i.e., the ratio of the thickness of the inner core in the cross sectional area parallel for the side of the tablet. In case that the ratio of the thickness of the inner core depends on the divided site, the highest ratio among the entire cross sectional surfaces is defined as "the ratio of the thickness of the inner core".

The ratio of the thickness of the inner core(%)=the thickness of the inner core(mm)/the thickness of the whole tablet(mm)×100

In the present invention, the porosity of the outer layer is preferably lowered to increase the hardness compared with a general tablet without an inner core. The porosity of the outer core is generally 1 to 40%, and preferably 1 to 30%.

The present invention is further illustrated in the followings.

(1) Outer Layer
(a) Microcrystalline Cellulose

Microcrystalline cellulose used herein as an essential ingredient of the outer layer is not limited to any specific one as long as it can be orally administrated. A preferred mean particle size of microcrystalline cellulose used as a starting material is 150 μm or less, more preferably 130 μm or less, and even more preferably 120 μm or less from the aspect of the feeling in oral cavity, since a formulation prepared by using microcrystalline cellulose with a large mean particle size brings sandy feeling in oral cavity after oral disintegration. The content of microcrystalline cellulose used herein is generally 5 to 80 wt % per the total weight of the outer layer, preferably 9 to 70 wt %, and more preferably 20 to 50 wt %, from the aspect of the hardness, the disintegrating time and the acceptable range of the compressive force. Examples of microcrystalline cellulose used herein include CEOLUS™ (PH-101, PH-102, PH-301, PH-302, PH-F20J, KG-800, KG-1000, ST-02: manufactured by Asahi Kasei Chemicals Co., Ltd.), and AVICEL™ (PH-101, PH-102, PH-301, PH-302, FD-101, FD-301, FD-F20: manufactured by FMC BioPolymer Co., Ltd). The microcrystalline cellulose used herein may be any one kind of them or a combination of two or more kinds thereof.

(b) Inorganic Excipient

The inorganic excipient used herein as an essential ingredient of the outer layer includes calcium hydrogen phosphates, magnesium carbonate, magnesium silicate, magnesium hydroxide, dried aluminum hydroxide gel, magnesium oxide, synthetic aluminum silicate, synthetic hydrotalcite, sodium bicarbonate, magnesium aluminometasilicate, magnesium aluminosilicate, calcium carbonate, precipitated calcium carbonate, talc, magnesia alumina hydrate, calcium silicate, dried aluminum hydroxide and magnesium carbonate mixed gel, coprecipitation product of aluminum hydroxide and sodium bicarbonate, coprecipitation product of aluminum hydroxide, calcium carbonate and magnesium carbonate, and coprecipitation product of aluminum hydroxide and aluminum potassium sulfate. Preferably, the inorganic excipient used herein includes calcium hydrogen phosphates, magnesium carbonate, magnesium silicate, magnesium hydroxide, dried aluminum hydroxide gel, magnesium oxide, synthetic aluminum silicate, synthetic hydrotalcite, and sodium bicarbonate, and more preferably, calcium hydrogen phosphates, magnesium carbonate, magnesium silicate, magnesium hydroxide, dried aluminum hydroxide gel, magnesium oxide, and synthetic aluminum silicate, and even more preferably, calcium hydrogen phosphates, magnesium silicate, dried aluminum hydroxide gel, magnesium oxide, synthetic aluminum silicate. The most preferred inorganic excipient among the above-listed ones is calcium hydrogen phosphates, in particular, calcium hydrogen phosphate (dicalcium phosphate), calcium hydrogen phosphate anhydrate (dicalcium phosphate anhydrate), and monobasic calcium phosphate (monocalcium phosphate). The inorganic excipient used herein may be any one kind of them or a combination of two or more kinds thereof. The content of the inorganic excipient used herein is a range of 10 to 80 wt % per the total weight of the outer layer, preferably 20 to 80 wt %, and more preferably 30 to 60 wt %, from the aspect of the hardness, the disintegrating time and the acceptable range of the compressive force.

(c) The Particular Ingredient

The particular ingredient as an essential ingredient of the outer layer of the present invention are characterized by using at least one ingredient selected from the group consisting of crospovidone, starches, low substituted hydroxypropyl-cellulose and carmellose. A press-coated orally-disintegrating tablet without the particular ingredient (described below) or a press-coated orally-disintegrating tablet with an ingredient for increasing the disintegratability other than the above particular ingredient cannot have the desired effects, since the porosity of the outer layer of the press-coated orally-disintegrating tablet need to be lowered to increase the hardness of the outer layer compared with a normal tablet without an inner core. In contrast, we have found that the desired effects can be achieved when the outer layer comprises the particular ingredient in combination with microcrystalline cellulose and inorganic excipients.

(c-1) Crospovidone

Crospovidone used herein is not specifically limited, but in general crospovidone adapted to the Japanese Pharmacopoeia may be used herein. A preferred mean particle size of crospovidone used as a starting material is, but not limited to, preferably 10 to 200 μm, more preferably 10 to 150 μm, and even more preferably 10 to 100 μm from the aspect of the feeling in oral cavity, since a formulation prepared by using crospovidone with a large mean particle size brings sandy feeling in oral cavity after oral disintegration. In order to achieve the desired particle size, crospovidone may be optionally milled with, for example, an airflow mill or a hammer mill. The content of crospovidone used in the outer layer is generally a range of 1 to 40 wt % per the total weight of the outer layer, preferably 1 to 30 wt %, more preferably 1 to 20 wt %, even more preferably 1 to 10 wt %, and the most preferably 1 to 5 wt %, from the aspect of the hardness, the disintegrating time and the acceptable range of the compressive force.

(c-2) Starches

Starches used herein may be include corn starch, potato starch, rice starch, wheat starch, sweet potato starch, mung bean starch, tapioca starch, and partly pregelatinized starch, and, preferably corn starch. In the present invention, completely-pregelatinized starch cannot be applied due to its poor disintegratability. These starches used herein may be any one kind of them or a combination of two or more kinds thereof. The mean particle size of starches is, but not limited to, preferably 10 to 200 μm, more preferably 10 to 100 μm, and even more preferably 10 to 50 μm, from the aspect of the feeling in oral cavity, since a formulation prepared by using starches with a large mean particle size brings sandy feeling in oral cavity after oral disintegration. In order to achieve the desired particle size, starches may be optionally milled with, for example, an airflow mills or a hammer mill. From the aspect of the hardness, the disintegrating time and the acceptable range of the compressive force, the content of starches is a range of 1 to 40 wt per the total weight of the outer layer. Too much content of the starches leads to a reduced fluidity and a poor productivity in the compression. Thus, the content of starches is generally a range of 1 to 40 wt % per the total weight of the outer layer, preferably 1 to 30 wt %, more preferably 1 to 20 wt %, even more preferably 1 to 10 wt and the most preferably 1 to 5 wt %.

(c-3) Low Substituted Hydroxypropylcellulose (L-HPC)

The degree of substitution in low substituted hydroxypropylcellulose of the present invention is not limited as long as it is adapted to the Japanese Pharmacopoeia, and generally the degree is a range of 7.0 to 12.9%. The mean particle size of low substituted hydroxypropylcellulose used as a starting material is, but not limited to, preferably a range of 10 to 200 μm, more preferably 10 to 150 μm, even more preferably 10 to 100 μm from the aspect of the feeling in oral cavity, since a formulation prepared by using low substituted hydroxypropylcellulose with a large mean particle size brings sandy feeling in oral cavity after oral disintegration. In order to achieve the desired particle size, low substituted hydroxypropylcellulose may be optionally milled with, for example, an airflow mill or a hammer mill. The content of low substituted hydroxypropylcellulose used in the outer layer is a range of 1 to 40 wt % per the total weight of the outer layer, preferably 1 to 30 wt %, more preferably 1 to 20 wt %, even more preferably 1 to 10 wt %, and the most preferably 1 to 5 wt % from the aspect of the hardness, the disintegrating time and the acceptable range of the compressive force.

(c-4) Carmellose (CMC)

Carmellose used herein is not specifically limited, but, carmellose adapted to the Japanese Pharmacopoeia may be used herein. The mean particle size of carmellose used as a starting material is, but not limited to, preferably a range of 10 to 200 µm, more preferably 10 to 150 µm, and even more preferably 10 to 100 µm from the aspect of the feeling in oral cavity, since a formulation prepared by using carmellose with a large mean particle size brings sandy feeling in oral cavity after oral disintegration. In order to achieve the desired particle size, carmellose may be optionally milled with, for example, an airflow mill or a hammer mill. The content of carmellose used in the outer layer is a range of 1 to 40 wt % per the total weight of the outer layer, preferably 1 to 30 wt %, more preferably 1 to 20 wt %, even more preferably 1 to 10 wt %, and the most preferably 1 to 5 wt % from the aspect of the hardness, the disintegrating time and the acceptable range of the compressive force.

Among the particular ingredients described above, preferred examples thereof include crospovidone, starches and low substituted hydroxypropylcellulose; more preferably crospovidone and starches; and even more preferably crospovidone and corn starch. From the aspect of the balance of hardness and disintegratability, the most preferred example of the particular ingredients is crospovidone. The content of a particular ingredient or the total content of particular ingredients used herein is generally a range of 2 to 40 wt % per the total weight of the outer layer, preferably 2 to 30 wt %, more preferably 2 to 20 wt %, even more preferably 2 to 10 wt %, and the most preferably 2 to 5 wt % from the aspect of the hardness, the disintegrating time and the acceptable range of the compressive force.

Additional Formulation Ingredients

Additional formulation ingredients can be added to the outer layer of the present orally-disintegrating tablet besides the ingredients described above. With regard to the "additional formulation ingredients" in the invention, any formulation ingredients can be used herein as long as the ingredients give no or little influence on the hardness and the disintegrating time of the tablet without any trouble on formulation. Examples of the additional ingredients used herein include other fillers, disintegrants, binders, sweetening agents, taste correctives/odor correctives, stabilizer, surfactant, fluidizing agents, antistatic agents, coating agents, lubricants, colorants, flavors and the like. The content of the "additional formulation ingredients" is a range of 0.01 to 25 wt % per the total weight of the outer layer, and each content of the above essential ingredients is reduced corresponding to the amount of these additional ingredients in the tablet.

Lubricant

In the present invention, it is preferable that the tablet comprises a lubricant among the above additional formulation ingredients in its outer layer. Examples of the lubricant include stearic acid, metallic stearate, sodium stearyl fumarate, sucrose ester of fatty acid, talc, hydrogenated oil, and macrogol. Examples of metallic stearate include magnesium stearate, calcium stearate and aluminum stearate and the like, and among lubricants, stearic acid, metallic stearate, and in particular magnesium sterate are preferable. The mean particle size of lubricant before the formulation process is a range of 0.5 to 50 µm and preferably 1 to 30 µm. The content of the lubricant is generally a range of 0.01 to 2.5 wt % per the total weight of the outer layer, preferably 0.01 to 2 wt %, and even more preferably 0.01 to 1 wt %. In the present invention, the lubricant can be added to the formulation either by external lubricating methods or internal lubricating methods.

(2) Inner Core

In the present invention, the inner core is not specifically limited as long as the inner core has a good oral disintegration and dispersibility. The outer layer of the present invention can give a sufficient hardness as the whole tablet even when the inner core of the tablet is poor formable, thus the present invention are also effective for a tablet containing the inner core comprising a "powder/granular material with poor formability". The "powder/granular material with poor formability" means a powder/granular material containing a powder and/or a granulated material with poor formability, and it also means that it is impossible to give a pressed substance or a pressed substance with an extremely low hardness is given even if the compression succeeds. In detail, it means that when the substance (50 mg) is compressed into tablet (diameter 6 mm) at a pressure of 4 kN, it is impossible to give a pressed substance or a pressed substance with an extremely low hardness (10 N or less) is given even if the compression succeeds. The mean particle size of the "powder/granular material with poor formability" used herein is, but not limited to, generally 3 mm or less, preferably 1 mm or less from the aspect of the feeling in oral cavity, even more preferably 300 µm or less, and the most preferably 150 µm or less. In the present invention, it is preferable that the inner core comprises an active ingredient, for example, including functional particle (such as small capsule and coated granule) containing an active ingredient; powder of an active ingredient; or mixed powders or granulated material which is prepared by adding additives to the said functional particle (such as small capsule and coated granule) containing an active ingredient, or powder of an active ingredient to improve the fluidity, the dispersibility and the adherability.

The said granulated material may be prepared by a fluidized bed granulation, an extrusion method, a dry-process compression and granulating method, a rotor granulation method, a rotor fluidized-bed granulation method, a high-speed mixer granulating method, and a fracturing granulation method.

The functional particles comprising an active ingredient can be prepared according to the procedures described in, for example, JP 3 (1991)-130214 A, JP 2007-63263 A, WO 2005/055989, and JP 2002-332226 A. In detail, a small capsule among the functional particles includes, for example, microcapsules in the broad sense of the term, such as microcapsules, seamless capsules, mini soft capsules, and microspheres.

A coated granule among the functional particle includes, for example, polymer-coated granules, wax-coated granules, and sugar-coated granules. It also includes a particle which might be inactivated by a high-pressure tableting, such as enzyme-containing granules. The various coated particles described above include, for example, granules prepared by coating granular particles with coating layer, granules comprising a core in their granular particles, and granules by coating granules comprising a core in their granular particles; which are designed to improve the sustained release, enteric solubility, gastric solubility, heat resistance, light resistance, stability or bitter taste. In the present invention, the term "coated" or "coating" includes coating the whole or a part of the surface of an active ingredient with a coating material. As apparatuses for this coating, ordinary fluidized-bed granulating machine (including rotor fluidized-bed granulating machine, Wurster fluidized-bed granulating machine and the like) can be mentioned; to suppress particle coarsening in a step, preference is given to improved Wurster fluidized-bed granulating machines equipped with an apparatus for forced circulation from side (for example, SPC, manufactured by POWREX CORPORATION, and the like), hybrid fluidized-bed granulating machines equipped with a grinding mechanism (screen impeller type, blade stator type, cross-screws, lump breakers and the like) (for example, super fine particle coating and granulating processor SFP-01, manufactured by POWREX CORPORATION, and the like), and rotary fluidized-bed granulating machines (for example, OMNITECS, manufactured by NARA MACHINERY CO. LTD., and the like). As apparatuses for spray drying, ordinary spray dryers (manufactured by OKAWARA CORPORATION, manufactured by OHKAWARA KAKOKI CO. LTD., manufactured by Yamato, manufactured by Niro, and the like) can be used.

The material of the inner core used for the preparation of the functional particles described above includes, for example, commercially available microcrystalline cellulose spheres, sucrose-starch spherical granules, purified sucrose spherical granules, lactose-crystalline cellulose spherical granules, D-mannitol, dibasic calcium phosphate anhydrate, magnesium oxide, magnesium hydroxide and the like.

Active Ingredient

The active ingredient used in the orally-disintegrating tablet of the present invention is not specifically limited as long as the active ingredient is served as a pharmaceutical active ingredient for the treatment and the prevention of diseases and is orally administrable. The active ingredient includes, for example, alimentary roborants; antipyretic analgesic antiphlogistics; psychotropic agents; hypnotics; antispasmodics; central nervous system acting drugs; cerebral metabolism improving agents; cerebral circulation improving antiepileptics; sympathomimetics; digestants; agents; antiulcer agents; prokinetic agents; antacids; antitussive expectorants; antimotility agents; antiemetics; respiratory stimulants; bronchodilators; antiallergic agents; cardiacs; antiarrhythmic agents; diuretics; vasoconstrictor; coronary vasodilators; vasodilator agents; peripheral vasodilators; antihyperlipemic drugs; cholagogues; chemotherapeutics; drugs for diabetic complications; osteoporosis treating drugs; antirheumatics; skeletal muscle relaxants; gout suppressant; anticoagulants; antineoplastic agents and the like. The active ingredient used herein may be in a salt thereof or in free form as long as it is pharmaceutically acceptable. Also, it may be in form of a solvate such as alcoholate, and hydrate. Furthermore, the above active ingredient may be used alone or in a combination of two or more kinds thereof.

When the inner core in the present invention comprises an active ingredient, the content of the active ingredient in the inner core is, but not specifically limited to, 0.1 to 100 wt per the total weight of the inner core, and preferably 1 to 95 wt %. The "content of an active ingredient in the inner core" in the present invention is based on a form of a "pharmaceutical active ingredient" generally employed as a drug, i.e., in case of a drug in a salt form, it is based on the amount of the salt. Also, the above active ingredient can be added to the outer layer to the extent to have no or little action on the hardness and the orally-disintegrating time of the final formulation.

(3) Preparation of Press-Coated Orally-Disintegrating Tablet

The press-coated orally-disintegrating tablet of the present invention can be prepared using a known tableting machine capable of preparing a press-coated formulation. A press-coated orally-disintegrating tablet containing a large amount of microcapsule-like functional particle in its inner core can be prepared using a tableting machine for press-coated formulation disclosed in WO2005/097041, etc., or a similar tableting machine or method for a preparation of press-coated formulation with a poor formable inner core.

The laboratory procedure of the present invention includes the following:

A mixture of the ingredients (a)-(c) described above is placed in a die whose diameter corresponds to that of the desired inner core, and the die is gently shaken to smooth the surface of the powder (which is the under-portion of the outer layer). On the mixture, a suitable amount of a powder/granular material with poor formability as an ingredient for the inner core is put, and the layered material is temporarily pressed at a relatively low pressure using a hand press machine. This temporarily-pressed substance is placed on a punch whose diameter corresponds to that of the final formulation concentrically in a manner to make the under-portion of the outer layer placed downward. A die is covered thereon, and a suitable amount of the additional above-mentioned mixture of the ingredients of the outer layer (for the side- and upper-portions of the outer layer) is put on the temporarily-pressed substance. The composition between the die and the punch is finally pressed into tablet to prepare a press-coated orally-disintegrating tablet.

Another example of the procedure includes the following:

A mixture of the ingredients (a)-(c) described above is placed in a die whose diameter corresponds to that of the desired tablet and temporarily pressed at a relatively low pressure using a hand press machine. Additionally, a powder/granular material with poor formability as an ingredient for the inner core is placed in a die whose diameter corresponds to that of the inner core and temporarily pressed at a relatively low pressure using a hand press machine. The temporarily-pressed substance for the inner core is placed concentrically on the temporarily-pressed material for the outer layer described above. A die is covered thereon, and a suitable amount of the additional above-mentioned mixture of the ingredients of the outer layer is put on the temporarily-pressed substance. The composition between the die and the punch is finally pressed into tablet to prepare a press-coated orally-disintegrating tablet.

The material of the outer layer may be prepared as a granule before tableting according to a known method in the art. For example, a press-coated formulation may be prepared using a homogenous mixture of the above ingredients (a)-(c) according to the method described above. Also, each ingredient of above (a)-(c) is granulated prior to the tableting, a lubricant is added to a mixture of the granulated ingredients, and then a press-coated formulation may be prepared using the obtained mixture according to the method described above. Furthermore, portions of each ingredient of above (a)-(c) are granulated prior to the tableting, the rest of the ingredients of (a)-(c) and a lubricant were added to a mixture of the granulated ingredients, and then a press-coated formulation may be prepared using the obtained mixture according to the method described above. The granulating method includes, for example, a fluidized bed granulation, an extrusion method, a dry-process compression and granulating method, a rotor granulation method, a rotor fluidized-bed granulation method, a high-speed mixing/granulating method, and a fracturing granulation method.

(4) Press-Coated Orally-Disintegrating Tablet

The press-coated orally-disintegrating tablet prepared as described above means a formulation which is administrable without water and shows a rapid disintegration in oral cavity. In detail, the orally-disintegrating tablet of the present invention means a formulation which is orally-disintegratable mainly by saliva within approximately 60 sec, generally 45 sec, and preferably 30 sec.

Also, the orally-disintegrating tablet of the present invention has a sufficient hardness not to chip or crack during the manufacturing process or the transportation. In detail, the absolute hardness of the orally-disintegrating tablet of the present invention is 1.5 N/mm² or more, and preferably 2.0 N/mm² or more.

The shape of the press-coated orally-disintegrating tablet which is the final formulation of the present invention may be, but not specifically limited to, a round-shaped tablet, a round-shaped R-tablet, a round-shaped tablet with angular corners, various irregular-shaped tablets and the like. The diameters of the round-shaped tablet, the round-shaped R-tablet, and the round-shaped beveled edge tablet of the present invention are generally 5-16 mm, and preferably 7-10 mm.

In the present invention, the "percentage of the thickness of the inner core" is generally 10-90%, preferably 20-80%, and more preferably 30-80%. Also, in the present invention, the thickness of the outer layer is generally 0.3-1.5 mm, and preferably 0.4-1.0 mm.

In the present invention, the percentage of the volume of the inner core per the total volume of the final formulation is 10-80%, and preferably 20-70%.

The press-coated orally-disintegrating tablet of the present invention should satisfy the oral disintegratability and the hardness enough to maintain its form as a formulation during the manufacturing process, the distribution process and the handling in medical practice settings and the like. The outer layer is required to have a sufficient hardness since the present invention is characterized in that the formulation of the present invention contains a powder/granular material with poor formability as its inner core. In addition, the higher hardness of the outer layer is required compared with that of a conventional orally-disintegrating tablet without a core. The lower porosity of the outer layer is preferable compared with that of a conventional tablet so that the sufficient hardness can be achieved. The porosity of outer layer of the tablet of the present invention is preferably 1-40%, and more preferably 1 to 30%.

EXAMPLES

Hereinafter, the present invention is further illustrated with the following examples, but should not be construed to be limited thereto.

Unless otherwise indicated, calcium hydrogen phosphate, corn starch, magnesium stearate, carmellose, low substituted hydroxypropylcellulose (L-HPC), microcrystalline cellulose spheres, microcrystalline cellulose, crospovidone and talc used in Examples are as follows: Calcium hydrogen phosphate anhydrate (GS: manufactured by Kyowa chemical Co., Ltd.), corn starch ((XX16)W: manufactured by Nihon Shokuhin Kako Co., Ltd), magnesium stearate (light and vegetative: manufactured by Taihei Chemical Industrial Co., Ltd.), carmellose (NS-300: manufactured by Gotoku Chemical Co., Ltd), low substituted hydroxypropylcellulose (LH-21: manufactured by Shin-Etsu Chemical Co., Ltd), microcrystalline cellulose spheres (CELPHERE® CP-203: manufactured by Asahi KASEI Chemicals Co., Ltd.), microcrystalline cellulose (CEOLUS® PH-101 or CEOLUS® PH-301: manufactured by Asahi KASEI Chemicals Co., Ltd.), crospovidone (Kollidon®CL: manufactured by BASF Japan Ltd., or Polyplasdone XL-10: manufactured by ISP Japan Ltd.), talc (manufactured by Hayashi-Kasei Co., Ltd.), erythritol (fine powder: manufactured by Nikken Chemical Co., Ltd.).

Examples 1-1 to 1-4

Study of the Particular Ingredients

<Preparation of Press-Coated Orally-Disintegrating Tablets>

Four formulations with different outer layer comprising each particular ingredient shown in Table 1-1 were prepared according to the formulae shown in the table. Firstly, the ingredients of each outer layer were mixed. A portion of each mixture (40 mg) was placed in a die (6 mm diameter), and the die was gently shaken to smooth the surface of the powder (which is the under-portion of the outer layer). On the mixture, 50 mg of microcrystalline cellulose spheres (CELPHERE, CP-203) as an ingredient for the inner core was put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 10 kN to prepare the desired press-coated orally-disintegrating tablets. In addition, the hardness of a pressed tablet (50 mg) prepared by pressing only the microcrystalline cellulose spheres (CELPHERE CP-203) used herein at a pressure of 4 kN in a punch/die (6 mm diameter) was less than 10 N.

TABLE 1-1

| | | Formula (mg) | | | |
|---|---|---|---|---|---|
| | | Example 1-1 | Example 1-2 | Example 1-3 | Example 1-4 |
| Inner core | Microcrystalline cellulose spheres (CELPHERE CP-203) | 50.00 | 50.00 | 50.00 | 50.00 |
| Outer layer | Microcrystalline cellulose (CEOLUS PH-101) | 64.22 | 64.22 | 64.22 | 64.22 |
| | Calcium hydrogen phosphate GS | 96.34 | 96.34 | 96.34 | 96.34 |
| | Carmellose (NS-300) | 18.00 | — | — | — |
| | Corn starch | — | 18.00 | — | — |
| | L-HPC (LH-21) | — | — | 18.00 | — |
| | Crospovidone (Kollidon CL) | — | — | — | 18.00 |
| | Magnesium stearate | 1.44 | 1.44 | 1.44 | 1.44 |
| | Total | 230.0 | 230.0 | 230.0 | 230.0 |

TABLE 1-2

| | | Formulation ratio in the outer layer (wt %) | | | |
|---|---|---|---|---|---|
| | | Example 1-1 | Example 1-2 | Example 1-3 | Example 1-4 |
| Outer layer | Microcrystalline cellulose (CEOLUS PH-101) | 35.7 | 35.7 | 35.7 | 35.7 |
| | Calcium hydrogen phosphate GS | 53.5 | 53.5 | 53.5 | 53.5 |
| | Carmellose (NS-300) | 10.0 | — | — | — |
| | Corn starch | — | 10.0 | — | — |
| | L-HPC (LH-21) | — | — | 10.0 | — |
| | Crospovidone (Kollidon CL) | — | — | — | 10.0 |
| | Magnesium stearate | 0.8 | 0.8 | 0.8 | 0.8 |
| | Total | 100.0 | 100.0 | 100.0 | 100.0 |

The orally-disintegrating time, hardness, and thickness of the product tablets were measured and the absolute hardness, HDBI and porosity thereof were calculated. The results were tabulated in Table 1-3 to show the physical properties of the product tablets. As described in Examples 1-1 to 1-4, in case that the outer layers of the tablets comprise any one of carmellose, corn starch, L-HPC, or crospovidone, the orally-disintegrating time of 30 sec or short and the absolute hardness of 1.5 N/mm² or more were achieved to give a high HDBI which is an index of the balance of hardness and disintegratability. Also, in each formula, the feeling in buccal cavity was satisfactory without feeling an oral dryness. The HDBI was the highest when crospovidone was used as the particular ingredient. All the porosities in each outer layer were less than 30%.

TABLE 1-3

Physical properties of the tablets

|  | Example 1-1 | Example 1-2 | Example 1-3 | Example 1-4 |
|---|---|---|---|---|
| Orally-disintegrating time (sec) | 15 | 14 | 17 | 10 |
| Absolute hardness (N/mm²) | 4.2 | 4.2 | 5.0 | 4.2 |
| HDBI | 0.29 | 0.29 | 0.29 | 0.42 |
| Porosity in the outer layer (%) | 26 | 24 | 27 | 28 |

Comparative Examples 1-1 to 1-2

Tablets without the Particular Ingredient (1)

A formulation without the particular ingredient in its outer layer (Comparative Example 1-1) and a formulation comprising croscarmellose sodium in its outer layer instead of the particular ingredient (Comparative Example 1-2) were prepared as described in Example 1-1 according to the formulae shown in Table 2-1. Ac-Di-Sol (manufactured by DSP Gokyo Food and Chemical Co., Ltd.) was used as croscarmellose sodium.

TABLE 2-1

Formula (mg)

|  |  | Example 1-1 | Example 1-2 |
|---|---|---|---|
| Inner core | Microcrystalline cellulose spheres (CELPHERE CP-203) | 50.00 | 50.00 |
| Outer layer | Microcrystalline cellulose (CEOLUS PH-101) | 71.42 | 64.22 |
|  | Calcium hydrogen phosphate GS | 107.14 | 96.34 |
|  | Croscarmellose Sodium | — | 18.00 |
|  | Magnesium stearate | 1.44 | 1.44 |
|  | Total | 230.0 | 230.0 |

TABLE 2-2

Formulation ratio in the outer layer (wt %)

|  |  | Comparative Example 1-1 | Comparative Example 1-2 |
|---|---|---|---|
| Outer layer | Microcrystalline cellulose (CEOLUS PH-101) | 39.7 | 35.7 |
|  | Calcium hydrogen phosphate GS | 59.5 | 53.5 |
|  | Croscarmellose Sodium | — | 10.0 |
|  | Magnesium stearate | 0.8 | 0.8 |
|  | Total | 100.0 | 100.0 |

The orally-disintegrating time, hardness, and thickness of the product tablets were measured and the absolute hardness, HDBI and porosity thereof were calculated. The results were tabulated in Table 2-3 to show the physical properties of the product tablets. As shown in the results of Comparative Examples 1-1 and 1-2 therein, in case that the outer layers of the tablet do not comprise the particular ingredient of the present invention, the orally-disintegrating time thereof was more than 30 sec though the porosity in the outer layers was similar to those of Example 1. The HDBI which is an index of the balance of hardness and disintegratability was low (not more than 0.15).

TABLE 2-3

Physical properties of the tablets

|  | Comparative Example 1-1 | Comparative Example 1-2 |
|---|---|---|
| Orally-disintegrating time (sec) | 63 | 69 |
| Absolute hardness (N/mm²) | 4.4 | 4.7 |
| HDBI | 0.07 | 0.07 |
| Porosity in outer layer (%) | 26 | 27 |

Comparative Example 1-3

Tablet without the Particular Ingredient (2) (The Outer Layer in Patent Reference 2)

A formulation without the particular ingredient of the present application and other ingredients was prepared according to the formula shown in Table 2-4 similar to Examples in Patent Reference 2 as described in Example 1-1 of the present application. Note that the die and punch used herein were applied with a small amount of magnesium stearate. Cellactose 80 (manufactured by MEGGLE co., Ltd.) was employed.

TABLE 2-4

Formula (mg)

|  |  | Comparative Example 1-3 |
|---|---|---|
| Inner core | Microcrystalline cellulose spheres (CELPHERE CP-203) | 50.00 |
| Outer layer | Cellactose 80 (granulated material of lactose and powdered cellulose) | 180.00 |
|  | Magnesium stearate | trace |
|  | Total | 230.0 |

TABLE 2-5

Formulation ratio in the outer layer (wt %)

|  |  | Comparative Example 1-3 |
|---|---|---|
| Outer layer | Cellactose 80 (granulated material of lactose and powdered cellulose) | 100.0 |
|  | Magnesium stearate | trace |
|  | Total | 100.0 |

The orally-disintegrating time, hardness and thickness of the product tablet were measured and the absolute hardness and HDBI thereof were calculated. The results were tabulated in Table 2-6 to show the physical properties of the product tablet. The product tablet did not orally disintegrate.

TABLE 2-6

| Physical properties of the tablets | |
| --- | --- |
| | Comparative Example 1-3 |
| Orally-disintegrating time (sec) | ≧120 |
| Absolute hardness (N/mm$^2$) | 3.7 |
| HDBI | ≦0.03 |

Comparative Example 1-4

Tablet without the Particular Ingredient (3) (the Outer Layer in Patent Reference 1)

A formulation without the particular ingredient in the outer layer was prepared as described in Example 1-1 according to the formula shown in Table 2-7. The formula of the outer layer was the same as the ratio described in Example 6 of Patent Reference 6 (60 mg of erythritol, 19.5 mg of microcrystalline cellulose, and 0.5 mg of magnesium stearate).

TABLE 2-7

| | Formula (mg) | |
| --- | --- | --- |
| | | Comparative Example 1-4 |
| Inner core | Microcrystalline cellulose spheres (CELPHERE CP-203) | 50.00 |
| Outer layer | Erythritol | 135.00 |
| | Microcrystalline cellulose (CEOLUS PH-102) | 43.90 |
| | Magnesium stearate | 1.10 |
| | Total | 230.0 |

TABLE 2-8

| | Formulation ratio in the outer layer (wt %) | |
| --- | --- | --- |
| | | Comparative Example 1-4 |
| Outer layer | Erythritol | 75.0 |
| | Microcrystalline cellulose (CEOLUS PH-102) | 24.4 |
| | Magnesium stearate | 0.6 |
| | Total | 100.0 |

The orally-disintegrating time, hardness and thickness of the product tablet were measured and the absolute hardness and HDBI thereof were calculated. The results were tabulated in Table 2-9 to show the physical properties of the product tablet. When press-coated tablet containing unformable particles was prepared according to the outer layer described in Example 6 of Patent Reference 1, the orally-disintegrating time thereof was short, but the absolute hardness thereof was insufficient and low (less than 1 N/mm$^2$). Thus, it was concluded that a sufficient hardness of the whole tablet can not be achieved by using the ingredients disclosed in Patent Reference 1 in the outer layer when press-coated tablet containing unformable particles was prepared.

TABLE 2-9

| Physical properties of the tablets | |
| --- | --- |
| | Comparative Example 1-4 |
| Orally-disintegrating time (sec) | 12 |
| Absolute hardness (N/mm$^2$) | 0.4 |
| HDBI | 0.03 |

Examples 2-1 to 2-5

Investigation of Ratio of Microcrystalline Cellulose (1)

Five formulations with different amount of microcrystalline cellulose in the outer layer were prepared according to the formulae shown in Table 3-1 as described in Example 1-1 herein. The final compression into tablet was carried out at a pressure of 8 kN in Example 2-2, 15 kN in Example 2-4, and 10 kN in other Examples.

TABLE 3-1

| | | Formula (mg) | | | | |
| --- | --- | --- | --- | --- | --- | --- |
| | | Example 2-1 80% | Example 2-2 69.2% | Example 2-3 35.7% | Example 2-4 9.2% | Example 2-5 5% |
| Inner core | Microcrystalline cellulose spheres (CELPHERE CP-203) | 50.00 | 50.00 | 50.00 | 50.00 | 50.00 |
| Outer layer | Microcrystalline cellulose (CEOLUS PH-101) | — | 124.56 | 64.22 | 16.56 | — |
| | Microcrystalline cellulose (CEOLUS PH-301) | 144.00 | — | — | — | 9.00 |
| | Calcium hydrogen phosphate GS | 25.56 | 36.00 | 96.34 | 144.00 | 115.56 |
| | Corn starch | — | 18.00 | 18.00 | 18.00 | — |

TABLE 3-1-continued

| Formula (mg) | | | | | |
|---|---|---|---|---|---|
| | Example 2-1 80% | Example 2-2 69.2% | Example 2-3 35.7% | Example 2-4 9.2% | Example 2-5 5% |
| Crospovidone (Polyplasdone XL-10) | 9.00 | — | — | — | 54.00 |
| Magnesium stearate | 1.44 | 1.44 | 1.44 | 1.44 | 1.44 |
| Total | 230.0 | 230.0 | 230.0 | 230.0 | 230.0 |

TABLE 3-2

| | | Formulation ratio in the outer layer (wt %) | | | | |
|---|---|---|---|---|---|---|
| | | Example 2-1 80% | Example 2-2 69.2% | Example 2-3 35.7% | Example 2-4 9.2% | Example 2-5 5% |
| Outer layer | Microcrystalline cellulose (CEOLUS PH-101) | — | 69.2 | 35.7 | 9.2 | — |
| | Microcrystalline cellulose (CEOLUS PH-301) | 80.0 | — | — | — | 5.0 |
| | Calcium hydrogen phosphate GS | 14.2 | 20.0 | 53.5 | 80.0 | 64.2 |
| | Corn starch | — | 10.0 | 10.0 | 10.0 | — |
| | Crospovidone (Polyplasdone XL-10) | 5.0 | — | — | — | 30.0 |
| | Magnesium stearate | 0.8 | 0.8 | 0.8 | 0.8 | 0.8 |
| | Total | 100.0 | 100.0 | 100.0 | 100.0 | 100.0 |

The orally-disintegrating time, hardness and thickness of the product tablets were measured and the absolute hardness and HDBI thereof were calculated. The results were tabulated in Table 3-3 to show the physical properties of the product tablets. The percentages of the thickness of the inner core per the thickness of each the total tablet were 38% in Example 2-1, 34% in Example 2-2, 44% in Example 2-4, and 39% in Example 2-5.

In case that the percentage of microcrystalline cellulose in the outer layer was in the range of 5 to 80% as described in Examples 2-1 to 2-5, the orally-disintegrating time of 30 sec or short and the absolute hardness of 1.5 N/mm² or more were achieved to give a high HDBI which is an index of the balance of hardness and disintegratability.

TABLE 3-3

| Physical properties of the tablets | | | | | |
|---|---|---|---|---|---|
| | Example 2-1 80% | Example 2-2 69.2% | Example 2-3 35.7% | Example 2-4 9.2% | Example 2-5 5% |
| Orally-disintegrating time (sec) | 17 | 26 | 14 | 7 | 12 |
| Absolute hardness (N/mm$^2$) | 4.6 | 5.7 | 4.2 | 2.7 | 2.8 |
| HDBI | 0.27 | 0.22 | 0.29 | 0.37 | 0.23 |

Examples 2-6

Investigation of Ratio of Microcrystalline Cellulose (2)

A formulation comprising 59.2% microcrystalline cellulose and 30% inorganic excipient in its outer layer was prepared according to the formula shown in Table 3-4 as described in Example 1-1. The final compression into tablet was carried out at a pressure of 10 kN.

TABLE 3-4

| | | Formula (mg) |
|---|---|---|
| | | Example 2-6 |
| Inner core | Microcrystalline cellulose spheres (CELPHERE CP-203) | 50.00 |
| Outer layer | Microcrystalline cellulose (CEOLUS PH-101) | 106.60 |
| | Dicalcium phosphate anhydrous | 54.00 |
| | Corn starch | 18.00 |
| | Magnesium stearate | 1.44 |
| | Total | 230.0 |

TABLE 3-5

| | Formulation ratio in the outer layer (wt %) | |
|---|---|---|
| | | Example 2-6 59.2% |
| Outer layer | Microcrystalline cellulose (CEOLUS PH-101) | 59.2 |
| | Dicalcium phosphate anhydrous | 30.0 |
| | Corn starch | 10.0 |
| | Magnesium stearate | 0.8 |
| | Total | 100.0 |

The orally-disintegrating time, hardness and thickness of the product tablet were measured and the absolute hardness and HDBI thereof were calculated. The results were tabulated in Table 3-6 to show the physical properties of the product tablet. The percentage of the thickness of the inner core per the thickness of the total tablet was 31%.

The orally-disintegrating time of 30 sec or short and the absolute hardness of 1.5 N/mm² or more were achieved to give a high HDBI which is an index of the balance of hardness and disintegratability.

TABLE 3-6

| Physical properties of the tablet | |
|---|---|
| | Example 2-6 59.2% |
| Orally-disintegrating time (sec) | 17 |
| Absolute hardness (N/mm²) | 5.7 |
| HDBI | 0.33 |

Examples 3-1 to 3-3

Investigation of Ratio of Lubricant

Formulations with different amount of lubricant in the outer layer were prepared according to the formulae shown in Table 4-1 as described in Example 1-1 herein. The final compression into tablet was carried out at a pressure of 15 kN in Example 3-1 and 10 kN in other Examples.

TABLE 4-1

| | Formula (mg) | | | |
|---|---|---|---|---|
| | | Example 3-1 0.1% | Example 3-2 0.8% | Example 3-3 1.6% |
| Inner core | Microcrystalline cellulose spheres (CELPHERE CP-203) | 50.00 | 50.00 | 50.00 |
| Outer layer | Microcrystalline cellulose (CEOLUS PH-101) | 64.73 | 64.22 | 63.65 |
| | Calcium hydrogen phosphate GS | 97.09 | 96.34 | 95.47 |
| | Corn starch | 18.00 | 18.00 | 18.00 |
| | Magnesium stearate | 0.18 | 1.44 | 2.88 |
| | Total | 230.0 | 230.0 | 230.0 |

TABLE 4-2

| | Formulation ratio in the outer layer (wt %) | | | |
|---|---|---|---|---|
| | | Example 3-1 0.1% | Example 3-2 0.8% | Example 3-3 1.6% |
| Outer layer | Microcrystalline cellulose (CEOLUS PH-101) | 36.0 | 35.7 | 35.4 |
| | Calcium hydrogen phosphate GS | 53.9 | 53.5 | 53.0 |
| | Corn starch | 10.0 | 10.0 | 10.0 |
| | Magnesium stearate | 0.1 | 0.8 | 1.6 |
| | Total | 100.0 | 100.0 | 100.0 |

The orally-disintegrating time, hardness and thickness of the product tablets were measured and the absolute hardness and HDBI thereof were calculated. The results were tabulated in Table 4-3 to show the physical properties of the product tablets. In all tablets shown in Table 4-3, the orally-disintegrating time of 30 sec or short and the absolute hardness of 1.5 N/mm² or more were achieved to give a high HDBI which is an index of the balance between hardness and disintegration.

TABLE 4-3

| Physical properties of the tablets | | | |
|---|---|---|---|
| | Example 3-1 0.1% | Example 3-2 0.8% | Example 3-3 1.6% |
| Orally-disintegrating time (sec) | 10 | 14 | 14 |
| Absolute hardness (N/mm²) | 7.5 | 4.2 | 3.9 |
| HDBI | 0.72 | 0.29 | 0.28 |

Examples 4-1 to 4-4

Investigation of Ratio of the Particular Ingredient (Corn Starch)

Formulations with different amount of corn starch in the outer layer were prepared according to the formulae shown in Table 5-1 as described in Example 1-1 herein. The final compression into tablet was carried out at a pressure of 10 kN.

TABLE 5-1

| | Formula (mg) | | | | |
|---|---|---|---|---|---|
| | | Example 4-1 1% | Example 4-2 10% | Example 4-3 30% | Example 4-4 40% |
| Inner core | Microcrystalline cellulose spheres (CELPHERE CP-203) | 50.00 | 50.00 | 50.00 | 50.00 |
| Outer layer | Microcrystalline cellulose (CEOLUS PH-301) | 90.00 | — | 90.00 | 90.00 |
| | Microcrystalline cellulose (CEOLUS PH-101) | — | 64.22 | — | — |
| | Calcium hydrogen phosphate GS | 86.76 | 96.34 | 34.56 | 16.56 |

TABLE 5-1-continued

| | Formula (mg) | | | |
|---|---|---|---|---|
| | Example 4-1 1% | Example 4-2 10% | Example 4-3 30% | Example 4-4 40% |
| Corn starch | 1.80 | 18.00 | 54.00 | 72.00 |
| Magnesium stearate | 1.44 | 1.44 | 1.44 | 1.44 |
| Total | 230.0 | 230.0 | 230.0 | 230.0 |

TABLE 5-2

| | | Formulation ratio in the outer layer (wt %) | | | |
|---|---|---|---|---|---|
| | | Example 4-1 1% | Example 4-2 10% | Example 4-3 30% | Example 4-4 40% |
| Outer layer | Microcrystalline cellulose (CEOLUS PH-301) | 50.0 | — | 50.0 | 50.0 |
| | Microcrystalline cellulose (CEOLUS PH-101) | — | 35.7 | — | — |
| | Calcium hydrogen phosphate GS | 48.2 | 53.5 | 19.2 | 9.2 |
| | Corn starch | 1.0 | 10.0 | 30.0 | 40.0 |
| | Magnesium stearate | 0.8 | 0.8 | 0.8 | 0.8 |
| | Total | 100.0 | 100.0 | 100.0 | 100.0 |

The orally-disintegrating time, hardness and thickness of the product tablets were measured and the absolute hardness and HDBI thereof were calculated. The results were tabulated in Table 5-3 to show the physical properties of the product tablets. The percentages of the thickness of the inner core per the thickness of each the total tablet were 40% in Example 4-1, 39% in Example 4-3, and 38% in Example 4-4.

As shown in Comparative Example 1-1, the tablet without any corn starch in the outer layer did not orally disintegrate within 30 sec, while the tablets comprising 1% to 40% corn starch in the outer layer achieved the orally-disintegrating time of 30 sec or short and the absolute hardness of 1.5 N/mm$^2$ or more to give a high HDBI which is an index of the balance of hardness and disintegratability, as described in Examples 4-1 to 4-4. Thus, these results show that excellent press-coated orally-disintegrating tablets can be provided when the outer layers comprise 1 to 40% corn starch.

TABLE 5-3

| | Physical properties of the tablets | | | |
|---|---|---|---|---|
| | Example 4-1 1% | Example 4-2 10% | Example 4-3 30% | Example 4-4 40% |
| Orally-disintegrating time (sec) | 15 | 14 | 9 | 7 |
| Absolute hardness (N/mm$^2$) | 4.2 | 4.2 | 3.0 | 2.1 |
| HDBI | 0.29 | 0.29 | 0.34 | 0.28 |

Examples 5-1 to 5-4

Investigation of Ratio of the Particular Ingredient (Crospovidone)

Formulations with different amount of crospovidone in the outer layer were prepared according to the formulae shown in Table 6-1 as described in Example 1-1 herein. The final compression into tablet was carried out at a pressure of 10 kN.

TABLE 6-1

| | | Formula (mg) | | | |
|---|---|---|---|---|---|
| | | Example 5-1 1% | Example 5-2 10% | Example 5-3 20% | Example 5-4 30% |
| Inner core | Microcrystalline cellulose spheres (CELPHERE CP-203) | 50.00 | 50.00 | 50.00 | 50.00 |
| Outer layer | Microcrystalline cellulose (CEOLUS PH-301) | 90.00 | — | 90.00 | 90.00 |
| | Microcrystalline cellulose (CEOLUS PH-101) | — | 64.22 | — | — |
| | Calcium hydrogen phosphate GS | 86.76 | 96.34 | 52.56 | 34.56 |
| | Crospovidone | 1.80 | 18.00 | 36.00 | 54.00 |
| | Magnesium stearate | 1.44 | 1.44 | 1.44 | 1.44 |
| | Total | 230.0 | 230.0 | 230.0 | 230.0 |

TABLE 6-2

| | | Formulation ratio in the outer layer (wt %) | | | |
|---|---|---|---|---|---|
| | | Example 5-1 1% | Example 5-2 10% | Example 5-3 20% | Example 5-4 30% |
| Outer layer | Microcrystalline cellulose (CEOLUS PH-301) | 50.0 | — | 50.0 | 50.0 |
| | Microcrystalline cellulose (CEOLUS PH-101) | — | 35.7 | — | — |
| | Calcium hydrogen phosphate GS | 48.2 | 53.5 | 29.2 | 19.2 |
| | Crospovidone | 1.0 | 10.0 | 20.0 | 30.0 |
| | Magnesium stearate | 0.8 | 0.8 | 0.8 | 0.8 |
| | Total | 100.0 | 100.0 | 100.0 | 100.0 |

The orally-disintegrating time, hardness and thickness of the product tablets were measured and the absolute hardness and HDBI thereof were calculated. The results were tabulated in Table 6-3 to show the physical properties of the product tablets. The percentages of the thickness of the inner core per the thickness of each the total tablet were 44% in Example 5-1, 38% in Example 5-2, 38% in Example 5-3, 34% in Example 5-4.

As shown in Comparative Example 1-1, the tablet without any crospovidone in the outer layer did not orally disintegrate within 30 sec, while the tablets comprising 1% to 30% crospovidone in the outer layer achieved the orally-disintegrating time of 30 sec or short and the absolute hardness of 1.5 N/mm$^2$ or more to give a high HDBI which is an index of the balance of hardness and disintegratability, as described in Examples 5-1 to 5-4. Notably, the fewer content of crospovidone gave the higher HDBI.

TABLE 6-3

Physical properties of the tablets

|  | Example 5-1 1% | Example 5-2 10% | Example 5-3 20% | Example 5-4 30% |
|---|---|---|---|---|
| Orally-disintegrating time (sec) | 9 | 10 | 14 | 28 |
| Absolute hardness (N/mm²) | 4.9 | 4.2 | 4.7 | 5.3 |
| HDBI | 0.54 | 0.42 | 0.33 | 0.19 |

Examples 6-1 to 6-3

Investigation of Thickness of Inner Core (1)

Formulations in which the thickness of the inner core is different each other were prepared according to the formulae shown in Table 7-1. Firstly, the ingredients of the outer layer were mixed. The mixture of the outer layer in an amount indicated in each column of "Weight of outer layer (under-portion)" in Table 7-1 was placed in a die with a diameter indicated in each column of "Inner core" in table 0.7-1. The die was gently shaken to smooth the surface of the powder. On the mixture, the amount of microcrystalline cellulose spheres (CELPHERE CP-203) indicated in the table was put, and the layered material was temporarily pressed at a low pressure of 3 kN using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer in an amount indicated in each column of "Weight of outer layer (side- and upper-portions)" in Table 7-1 was added therein. The composition between the punch and the die was finally pressed to prepare the press-coated orally-disintegrating tablets. The final compression into tablet was carried out at a pressure of 15 kN.

TABLE 7-1

Formula (mg)

|  |  | Example 6-1 | Example 6-2 | Example 6-3 |
|---|---|---|---|---|
| Structure | Inner core | Diameter 6 mm | Diameter 7.5 mm | Diameter 6 mm |
|  | Weight of outer layer (under-portion) | 40 mg | 96 mg | 20 mg |
|  | Weight of outer layer (side- and upper-portions) | 140 mg | 84 mg | 90 mg |
| Inner core | Microcrystalline cellulose spheres (CELPHERE CP-203) | 50.00 | 50.00 | 120.00 |
| Outer layer | Microcrystalline cellulose (CEOLUS PH-101) | 64.73 | 64.73 | 39.56 |
|  | Calcium hydrogen phosphate GS | 97.09 | 97.09 | 59.33 |
|  | Corn starch | 18.00 | 18.00 | 11.00 |
|  | Magnesium stearate | 0.18 | 0.18 | 0.11 |
|  | Total | 230.0 | 230.0 | 230.0 |

TABLE 7-2

Formulation ratio in the outer layer (wt %)

|  |  | Example 6-1 | Example 6-2 | Example 6-3 |
|---|---|---|---|---|
| Outer layer | Microcrystalline cellulose (CEOLUS PH-101) | 36.0 | 36.0 | 36.0 |
|  | Calcium hydrogen phosphate GS | 53.9 | 53.9 | 53.9 |
|  | Corn starch | 10.0 | 10.0 | 10.0 |
|  | Magnesium stearate | 0.1 | 0.1 | 0.1 |
|  | Total | 100.0 | 100.0 | 100.0 |

The orally-disintegrating time, hardness and thickness of the product tablets were measured and the absolute hardness and HDBI thereof were calculated. The results were tabulated in Table 7-3 to show the physical properties of the product tablets. As described in Examples 6-1 to 6-3, in case that the percentage of the thickness of the inner core was in a range of 32 to 76%, the tablets achieved the orally-disintegrating time of 30 sec or short and the absolute hardness of 1.5 N/mm² or more to give a high HDBI which is an index of the balance of hardness and disintegratability.

TABLE 7-3

Physical properties of the tablets

|  | Example 6-1 | Example 6-2 | Example 6-3 |
|---|---|---|---|
| Orally-disintegrating time (sec) | 10 | 10 | 9 |
| Absolute hardness (N/mm2) | 7.5 | 8.2 | 3.4 |
| HDBI | 0.72 | 0.82 | 0.40 |
| Thickness of tablet (mm) | 2.75 | 2.70 | 2.94 |
| Thickness of inner core (mm) | 1.05 | 0.87 | 2.22 |
| Percentage of thickness of inner core (%) | 38 | 32 | 76 |

Examples 6-4 to 6-5

Investigation of Thickness of Inner Core (2)

Formulations in which the thickness of the inner core is different each other were prepared according to the formulae shown in Table 7-4. Firstly, the ingredients of the outer layer were mixed. The mixture of the outer layer in an amount indicated in each column of "Weight of outer layer (under-portion)" in Table 7-4 was placed in a die (8 mm diameter). The die was gently shaken to smooth the surface of the powder. On the mixture, the amount of microcrystalline cellulose spheres (CELPHERE CP-203) indicated in the table was put, and the layered material was temporarily pressed at a low pressure using a hand press machine (hydraulic press system, manufactured by RIKEN). This temporarily-pressed substance was placed on a punch (10 mm diameter) concentrically in a manner to make the under-portion of the outer layer placed downward. A die (10 mm diameter) was covered thereon, and the additional above-mentioned mixture of the ingredients of the outer layer in an amount indicated in each column of "Weight of outer layer (side- and upper-portions)" in Table 7-4 was added therein. The composition between the punch and the die was finally pressed to prepare the press-coated orally-disintegrating tablets. The final compression into tablet was carried out at a pressure of 8 kN in Example 6-4 and 15 kN in Example 6-5.

TABLE 7-4

Formula (mg)

| Structure | | Example 6-4 | Example 6-5 |
|---|---|---|---|
| | Tablet | Diameter 10 mm | Diameter 10 mm |
| | Inner core | Diameter 8 mm | Diameter 8 mm |
| | Weight of outer layer (under-portion) | 110 mg | 70 mg |
| | Weight of outer layer (side- and upper-portions) | 240 mg | 180 mg |
| Inner core | Microcrystalline cellulose spheres (CELPHERE CP-203) | 150.00 | 250.00 |
| Outer layer | Microcrystalline cellulose (CEOLUS PH-301) | 126.00 | 90.00 |
| | Dicalcium phosphate anhydrous | 188.65 | 134.75 |
| | Corn starch | 35.00 | 25.00 |
| | Magnesium stearate | 0.35 | 0.25 |
| | Total | 500.0 | 500.0 |

TABLE 7-5

Formulation ratio in the outer layer (wt %)

| | | Example 6-4 | Example 6-5 |
|---|---|---|---|
| Outer layer | Microcrystalline cellulose (CEOLUS PH-301) | 36.0 | 36.0 |
| | Dicalcium phosphate anhydrous | 53.9 | 53.9 |
| | Corn starch | 10.0 | 10.0 |
| | Magnesium stearate | 0.1 | 0.1 |
| | Total | 100.0 | 100.0 |

The orally-disintegrating time, hardness and thickness of the product tablet were measured and the absolute hardness and HDBI thereof were calculated. The results were tabulated in Table 7-6 to show the physical properties of the product tablets. As described in Examples 6-4 and 6-5, in case that the percentage of the thickness of the inner core was in a range of 32 to 76%, the tablets achieved the orally-disintegrating time of 30 sec or short and the absolute hardness of 1.5 N/mm² or more to give a high HDBI which is an index of the balance of hardness and disintegratability.

TABLE 7-6

Physical properties of the tablets

| | Example 6-4 | Example 6-5 |
|---|---|---|
| Orally-disintegrating time (sec) | 8 | 12 |
| Absolute hardness (N/mm²) | 2.3 | 1.9 |
| HDBI | 0.28 | 0.16 |
| Thickness of tablet (mm) | 4.42 | 4.28 |
| Thickness of inner core (mm) | 2.06 | 3.05 |
| Percentage of thickness of inner core (%) | 47 | 71 |

Comparative Example 2

Comparison of Physical Properties with Normal Tablet

A normal tablet in which unformable particles were homogenously distributed was prepared. Firstly, the ingredients shown in Table 7-7 were homogenously mixed in the ratio indicated in the table. The mixture was compressed into tablet (10 mm diameter) at a pressure of 8 kN to prepare a normal tablet. Note that the normal tablet was prepared in the same conditions as the press-coated tablet in Example 6-4, such as the amount of each ingredient per tablet, the weight of the tablet, the diameter of the tablet and the compressive force, except the different distribution of the unformable particle.

TABLE 7-7

Formula (mg)

| | Comparative Example 2 |
|---|---|
| Microcrystalline cellulose spheres (CELPHERE CP-203) | 150.00 |
| Microcrystalline cellulose (CEOLUS PH-301) | 126.60 |
| Dicalcium phosphate anhydrous | 188.65 |
| Corn starch | 35.00 |
| Magnesium stearate | 0.35 |
| Total | 500.0 |

TABLE 7-8

Formulation ration (wt %)

| | Comparative Example 2 |
|---|---|
| Microcrystalline cellulose spheres (CELPHERE CP-203) | 30.0 |
| Microcrystalline cellulose (CEOLUS PH-301) | 25.2 |
| Dicalcium phosphate anhydrous | 37.7 |
| Corn starch | 7.0 |
| Magnesium stearate | 0.1 |
| Total | 100.0 |

The orally-disintegrating time, hardness and thickness of the product tablets were measured and the absolute hardness and HDBI thereof were calculated. As shown in Table 7-9, the normal tablet had a lower absolute hardness and a longer orally-disintegrating time compared with those of the press-coated tablet.

Thus, regarding an orally-disintegrating tablet containing a large amount of unformable particles, it has been found that the press-coated tablet containing unformable particles in the inner core could achieve more preferable physical properties compared with the normal tablet in which the unformable particles were homogenously distributed.

TABLE 7-9

Physical properties of the tablet

| | Comparative Example 2 (normal tablet) | Example 6-4 (press-coated tablet) |
|---|---|---|
| Orally-disintegrating time (sec) | 17 | 8 |
| Absolute hardness (N/mm²) | 2.0 | 2.3 |
| HDBI | 0.12 | 0.28 |

Examples 7-1 to 7-3

Investigation of Porosity in Outer Layer

Formulations in which the porosity is different each other in the outer layer were prepared according to the formula shown in Table 8-1 as described in Example 1-1. The final compression into tablet was carried out at pressures of 6 kN, 10 kN and 15 kN.

TABLE 8-1

| | | Formula (mg) |
|---|---|---|
| | | Examples 7-1-7-3 |
| Inner core | Microcrystalline cellulose spheres (CELPHERE CP-203) | 50.00 |
| Outer layer | Microcrystalline cellulose (CEOLUS PH-101) | 64.22 |
| | Calcium hydrogen phosphate GS | 96.34 |
| | Corn starch | 18.00 |
| | Magnesium stearate | 1.44 |
| | Total | 230.0 |

TABLE 8-2

| | | Formulation ratio in the outer layer (wt %) |
|---|---|---|
| | | Examples 7-1 - 7-3 |
| Outer layer | Microcrystalline cellulose (CEOLUS PH-101) | 35.7 |
| | Calcium hydrogen phosphate GS | 53.5 |
| | Corn starch | 10.0 |
| | Magnesium stearate | 0.8 |
| | Total | 100.0 |

The orally-disintegrating time, hardness and thickness of the product tablets were measured and the absolute hardness, HDBI and porosity thereof were calculated. The results were tabulated in Table 8-3 to show the physical properties of the product tablets. The tablets achieved the orally-disintegrating time of 30 sec or short and the absolute hardness of 1.5 N/mm$^2$ or more to give a high HDBI which is an index of the balance of hardness and disintegratability. The tablets compressed at pressures ranging 6 kN to 15 kN had a suitable hardness and a disintegratability showing that an acceptable range of the compressing pressure is wide.

TABLE 8-3

| | Physical properties of the tablets | | |
|---|---|---|---|
| | Example 7-1 | Example 7-2 | Example 7-3 |
| Compressive force | 6 kN | 10 kN | 15 kN |
| Orally-disintegrating time (sec) | 10 | 14 | 25 |
| Absolute hardness (N/mm$^2$) | 2.2 | 4.2 | 5.4 |
| HDBI | 0.22 | 0.29 | 0.21 |
| Porosity in the outer layer (%) | 25 | 24 | 20 |

Example 8

Press-Coated Orally-Disintegrating Tablets Containing Active Ingredient (8-1) Press-Coated Tablet Containing Particle Comprising Acetaminophen 1) Preparation of Particle Comprising Acetaminophen (manufactured by Asahi Kasei Chemicals Co., Ltd.)

Acetaminophen was coated to prepare acetaminophen-containing particles whose coating-rate is 10 wt %. The coating material used herein comprises Aquacoat™ (manufactured by Asahi Kasei Chemical Co., Ltd), triacetin and mannitol in a ratio of 100:25:50 (wt %), respectively.

2) Preparation of Press-Coated Tablet

A formulation containing the acetaminophen-containing particles was prepared according to the formula shown in Table 9-1 as described in Example 1-1. The final compression into tablet was carried out at a pressure of 8 kN.

TABLE 9-1

| | | Formula (mg) |
|---|---|---|
| | | Example 8-1 |
| Inner core | Acetaminophen-containing particle | 28.6 |
| | Crospovidone (Polyplasdone XL-10) | 10.7 |
| | Talc | 10.7 |
| Outer layer | Microcrystalline cellulose (CEOLUS PH-101) | 64.22 |
| | Calcium hydrogen phosphate GS | 96.34 |
| | Crospovidone (Kollidon CL) | 18.00 |
| | Magnesium stearate | 1.44 |
| | Total | 230.0 |

TABLE 9-2

| | | Formulation ratio in the outer layer (wt %) |
|---|---|---|
| | | Example 8-1 |
| Outer layer | Microcrystalline cellulose (CEOLUS PH-101) | 35.7 |
| | Calcium hydrogen phosphate GS | 53.5 |
| | Crospovidone (Kollidon CL) | 10.0 |
| | Magnesium stearate | 0.8 |
| | Total | 100.0 |

3) Results

The orally-disintegrating time, hardness and thickness of the product tablet were measured and the absolute hardness and HDBI thereof were calculated. The results were tabulated in Table 9-3 to show the physical properties of the product tablet. The orally-disintegrating time of 30 sec or short and the absolute hardness of 1.5 N/mm$^2$ or more were achieved to give a high HDBI which is an index of the balance of hardness and disintegratability. Thus, it was also shown that preferable press-coated orally-disintegrating tablets could be prepared in case that they comprise an active ingredient.

TABLE 9-3

| Physical properties of the tablet | |
|---|---|
| | Example 8-1 |
| Orally-disintegrating time (sec) | 8 |
| Absolute hardness (N/mm$^2$) | 4.1 |
| HDBI | 0.51 |

(8-2) Press-Coated Tablet Containing Particle Comprising Famotidine

1) Preparation of Particle Comprising Famotidine

To 567 g of purified water was added 31.5 g of polysorbate 80 (Japanese Pharmacopoeia polysorbate 80 (HX): manufactured by NOF Co., Ltd.) and the mixture was well mixed. Then, 73.5 g of talc (manufactured by Hayashi Kasei Co., Ltd.) and 52.5 g of croscarmellose sodium (Ac-Di-Sol: manufactured by FMC BioPolymer Co., Ltd.) were added thereto and the solution was well stirred ("Solution I").

Additionally, another solution of sodium hydroxide (2.85 g) in purified water (67.65 g) was slowly added to 705 g of methacrylic copolymer LD (POLYQUID PA-30S: manufactured by Sanyo Chemical Industries Ltd.) and the solution was stirred ("Solution II"). To Solution I was added Solution II to be suspended. The suspension was sieved through a mesh (177 μm) to obtain a coating dispersion.

346.5 g of famotidine and 3.5 g of light anhydrous silicic acid (aerosil 200: manufactured by Nippon Aerosil Co., Ltd.) were separately sieved through a mesh (500 μm) and mixed well in a polyethylene bag to prepare a drug-containing composition. Then, the composition was sprayed with the coating dispersion prepared above in a Wurster-fluid bed granulator equipped with forced circulation device (improved Wurster-fluidized bet granulator, MP-01 SPC, manufactured by Powrex Co.). The spraying was performed at a inlet air temperature of 80 to 90° C. and the outlet air temperature of 26 to 30° C., and the production was performed while spraying the spray liquid from a bottom spray at a flow of 10-12 g/min, spray air flow of 80 L/min, spray air pressure of 0.2-0.3 MPa, side air pressure of 0.2-0.25 MPa, and inlet air flow of about 0.30-0.55 m$^3$/min. The coating was completed when the amount of coating dispersion was about 1306 g, and the resulting particles were dried until the outlet air temperature reached 42° C. The obtained particles were sieved through a 32 mesh (500 μm) sieve to prepare the famotidine-containing particles having a mean diameter of about 165 μm.

2) Preparation of Press-Coated Tablet

A formulation containing the particles comprising the active ingredient in the inner core was prepared according to the formula shown in Table 9-4. Mixed particles of the famotidine-containing particles and crospovidone and talc particles were used in the inner core. Firstly, the ingredients of the outer layer were mixed. A portion of the mixture (40 mg) was placed in a die (6 mm diameter) and the die was gently shaken to smooth the surface of the powder (which is the under-portion of the outer layer). On the mixture, 50 mg of the mixed particles of the inner core were put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 8 kN to prepare the desired press-coated orally-disintegrating tablets.

TABLE 9-4

| | Formula (mg) | |
|---|---|---|
| | | Example 8-2 |
| Inner core | Famotidine containing particle | 28.6 |
| | Crospovidone (Polyplasdone XL-10) | 10.7 |
| | Talc | 10.7 |
| Outer layer | Microcrystalline cellulose (CEOLUS PH-101) | 64.22 |
| | Calcium hydrogen phosphate GS | 96.34 |
| | Crospovidone (Kollidon CL) | 18.00 |
| | Magnesium stearate | 1.44 |
| | Total | 230.0 |

TABLE 9-5

| | Formulation ratio in the outer layer (wt %) | |
|---|---|---|
| | | Example 8-2 |
| Outer layer | Microcrystalline cellulose (CEOLUS PH-101) | 35.7 |
| | Calcium hydrogen phosphate GS | 53.5 |
| | Crospovidone (Kollidon CL) | 10.0 |
| | Magnesium stearate | 0.8 |
| | Total | 100.0 |

(8-3) Press-Coated Tablet Containing Particle Comprising Mosapride

1) Preparation of Particle Comprising Mosapride

Mosapride-containing particles were prepared as described in Example 8-2 using mosapride citrate instead of famotidine.

2) Preparation of Press-Coated Tablet

A formulation containing particles comprising mosapride in the inner core was prepared according to the formula shown in Table 9-6. Mixed particles of the mosapride-containing particles and crospovidone and talc particles were used in the inner core.

Firstly, the ingredients of the outer layer were mixed. A portion of the mixture (40 mg) was placed in a die (6 mm diameter) and the die was gently shaken to smooth the surface of the powder (which is the under-portion of the outer layer). On the mixture, 50 mg of the mixed particles of the inner core were put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 8 kN to prepare the desired press-coated orally-disintegrating tablets.

TABLE 9-6

| | Formula (mg) | |
|---|---|---|
| | | Example 8-3 |
| Inner core | Mosapride contining particle | 28.6 |
| | Crospovidone (Polyplasdone XL-10) | 10.7 |
| | Talc | 10.7 |

TABLE 9-6-continued

| | Formula (mg) | |
|---|---|---|
| | | Example 8-3 |
| Outer layer | Microcrystalline cellulose (CEOLUS PH-101) | 64.22 |
| | Calcium hydrogen phosphate GS | 96.34 |
| | Crospovidone (Kollidon CL) | 18.00 |
| | Magnesium stearate | 1.44 |
| | Total | 230.0 |

TABLE 9-7

| | Formulation ratio in the outer layer (wt %) | |
|---|---|---|
| | | Example 8-3 |
| Outer layer | Microcrystalline cellulose (CEOLUS PH-101) | 35.7 |
| | Calcium hydrogen phosphate GS | 53.5 |
| | Crospovidone (Kollidon CL) | 10.0 |
| | Magnesium stearate | 0.8 |
| | Total | 100.0 |

3) Results

The orally-disintegrating time, hardness and thickness of the product tablet were measured and the absolute hardness and HDBI thereof were calculated. The results were tabulated in Table 9-8 to show the physical properties of the product tablet. The orally-disintegrating time of 30 sec or short and the absolute hardness of 1.5 N/mm$^2$ or more were achieved to give a high HDBI which is an index of the balance of hardness and disintegratability. The taste derived from mosapride was masked and the feeling in oral cavity was good.

TABLE 9-8

| Physical properties of the tablet | |
|---|---|
| | Example 8-3 |
| Orally-disintegrating time (sec) | 15 |
| Absolute hardness (N/mm$^2$) | 5.2 |
| HDBI | 0.34 |

(8-4) Press-Coated Tablet Containing Enteric Particle
1) Particle Containing Enteric Particle Red particles in Contac 600ST capsule (Glaxo Smith Kline) were used as enteric particles.

2) Preparation of Press-Coated Tablet

A formulation containing the enteric particles in the inner core was prepared according to the formula shown in Table 9-9. Firstly, the ingredients of the outer layer were mixed. A portion of the mixture (40 mg) was placed in a die (6 mm diameter) and the die was gently shaken to smooth the surface of the powder (which is the under-portion of the outer layer). 50 mg of Contac 600ST particle (50 mg) was put onto the above powder and the die was gently shaken to smooth the surface of the layered material. Then, 20 mg of the additional above-mentioned mixture of the ingredients of the outer layer (for the upper-portion of the outer layer) was put onto the layered material, and the die was gently shaken to smooth the surface of the layered mixture. The layered mixture was temporarily pressed at a low pressure (1 kN) using a hand press machine (oil hydraulic press system, manufactured by RIKEN). This temporarily-pressed substance was placed on a punch (8 mm diameter) concentrically in manner to make the under-portion of the outer layer placed downward. A die (8 mm diameter) was covered thereon, and the additional above-mentioned mixture of the ingredients of the outer layer (for the side- and upper-portions of the outer layer, 120 mg) was put on the temporarily-pressed substance. The composition between the punch and the die was finally pressed at a pressure of 6 kN to prepare the desired press-coated orally-disintegrating tablets.

TABLE 9-9

| | Formula (mg) | |
|---|---|---|
| | | Example 8-4 |
| Inner core | Contac 600ST (sustained-release particle) | 50.00 |
| Outer layer | Microcrystalline cellulose (CEOLUS PH-301) | 64.80 |
| | Dicalcium phosphate anhydrous | 97.02 |
| | Crospovidone | 18.00 |
| | Magnesium stearate | 0.18 |
| | Total | 230.0 |

TABLE 9-10

| | Formulation ratio in the outer layer (wt %) | |
|---|---|---|
| | | Example 8-4 |
| Outer layer | Microcrystalline cellulose (CEOLUS PH-301) | 36.0 |
| | Dicalcium phosphate anhydrous | 53.9 |
| | Crospovidone | 10.0 |
| | Magnesium stearate | 0.1 |
| | Total | 100.0 |

3) Results

The orally-disintegrating time, hardness and thickness of the product tablet were measured and the absolute hardness and HDBI thereof were calculated. The results were tabulated in Table 9-11 to show the physical properties of the product tablet. The orally-disintegrating time of 30 sec or short and the absolute hardness of 1.5 N/mm$^2$ or more were achieved to give a high HDBI which is an index of the balance of hardness and disintegratability.

TABLE 9-11

| Physical properties of the tablet | |
|---|---|
| | Example 8-4 |
| Orally-disintegrating time (sec) | 5 |
| Absolute hardness (N/mm$^2$) | 2.4 |
| HDBI | 0.48 |
| Percentage of thickness of inner core (%) | 49 |

(8-5) Press-Coated Tablet Containing Famotidine Microcapsule
1) Famotidine Microcapsule The famotidine microcapsule used here was agar beads comprising 70% famotidine which was provided from Riken Vitamin Co., Ltd.

2) Preparation of Press-Coated Tablet

A formulation containing the microcapsules in the inner core was prepared according to the formula shown in Table 9-12. Mixed particles of the microcapsules and erythritol particles (fine powder: manufactured by Nikken Chemical Laboratory Co., Ltd.) were used as the inner core.

Firstly, the ingredients of the outer layer were mixed. A portion of the mixture (40 mg) was placed in a die (6 mm diameter) and the die was gently shaken to smooth the surface of the powder (which is the under-portion of the outer layer). On the mixture, 57.2 mg of the mixed particles of the inner core were put, and then the layered material was temporarily pressed at a low pressure (3 kN) using a hand press machine (oil hydraulic press system, manufactured by RIKEN). This temporarily-pressed substance was placed on a punch (8 mm diameter) concentrically in a manner to make the under-portion of the outer layer placed downward. A die (8 mm diameter) was covered thereon, and the additional above-mentioned mixture of the ingredients of the outer layer (for the side- and upper-portions of the outer layer, 140 mg) was put on the temporarily-pressed substance. The composition between the punch and the die was finally pressed at a pressure of 6 kN to prepare the desired press-coated orally-disintegrating tablets.

TABLE 9-12

| | Formula (mg) | |
|---|---|---|
| | | Example 8-5 |
| Inner core | 70% Famotidine containing microcapsule | 28.60 |
| | Erythritol | 28.60 |
| Outer layer | Microcrystalline cellulose (CEOLUS PH-301) | 64.80 |
| | Dicalcium phosphate anhydrous | 97.02 |
| | Crospovidone | 18.00 |
| | Magnesium stearate | 0.18 |
| | Total | 237.2 |

TABLE 9-13

| | Formulation ratio in the outer layer (wt %) | |
|---|---|---|
| | | Example 8-5 |
| Outer layer | Microcrystalline cellulose (CEOLUS PH-301) | 36.0 |
| | Dicalcium phosphate anhydrous | 53.9 |
| | Crospovidone | 10.0 |
| | Magnesium stearate | 0.1 |
| | Total | 100.0 |

3) Results

The orally-disintegrating time, hardness and thickness of the product tablet were measured and the absolute hardness and HDBI thereof were calculated. The results were tabulated in Table 9-14 to show the physical properties of the product tablet. The orally-disintegrating time of 30 sec or short and the absolute hardness of 1.5 N/mm$^2$ or more were achieved to give a high HDBI which represents an index of the balance between hardness and disintegratability.

TABLE 9-14

| Physical properties of the tablet | |
|---|---|
| | Example 8-5 |
| Orally-disintegrating time (sec) | 15 |
| Absolute hardness (N/mm$^2$) | 2.3 |

TABLE 9-14-continued

| Physical properties of the tablet | |
|---|---|
| | Example 8-5 |
| HDBI | 0.16 |
| Percentage of thickness of inner core (%) | 40 |

As shown above, press-coated tablets containing various inner cores, such as spherical particles (e.g., CELPHERE), particles coated with microparticles, enteric particles, and microcapsules can be prepared to provide press-coated orally-disintegrating tablets with a preferable balance between hardness and disintegratability.

INDUSTRIAL APPLICABILITY

The present invention can provide a press-coated orally-disintegrating tablet wherein its inner core has poor formability and which has a preferred balance between hardness and disintegratability.

The invention claimed is:

1. A press-coated orally-disintegrating tablet with an inner core which is a powder/granular material with poor formability and an outer layer surrounding the inner core wherein
   the inner core has a thickness in the range of 20 to 80% per that of the whole tablet, and
   the outer layer consisting of (a) microcrystalline cellulose, (b) one or more inorganic excipients selected from the group consisting of calcium hydrogen phosphate, calcium hydrogen phosphate anhydrate, and monobasic calcium phosphate, (c) one or more particular ingredients selected from the group consisting of crospovidone, starches and low substituted hydroxypropylcellulose, and (d) one or more additional formulation ingredients, wherein the one or more additional formulation ingredients (d) are one or two selected from the group consisting of fillers, disintegrants, binders, sweetening agents, taste correctives/odor correctives, stabilizer, surfactant, fluidizing agents, antistatic agents, coating agents, lubricants, colorants, and flavors,
   wherein the microcrystalline cellulose (a) is contained in the range of 5 to 80 wt % per 100 wt % of the outer layer,
   the total content of the inorganic excipient (b) is contained in the range of 30 to 60 wt % per 100 wt % of the outer layer,
   the total content of the one or more particular ingredients (c) is in the range of 1 to 40 wt % per 100 wt % of the outer layer, and
   the one or more additional formulation ingredients are contained in the range of 0.01 to 25 wt % per 100 wt % of the outer layer,
   wherein the absolute hardness of the press-coated orally-disintegrating tablet is 1.5 N/mm$^2$ or more.

2. The press-coated orally-disintegrating tablet of claim 1 wherein the starches are corn starch.

3. The press-coated orally-disintegrating tablet of claim 1 wherein the particular ingredients (c) are one or two selected from the group consisting of crospovidone and corn starch.

4. The press-coated orally-disintegrating tablet of claim 1 wherein the particular ingredients (c) are crospovidone.

5. The press-coated orally-disintegrating tablet of claim 1 wherein the porosity in the outer layer is 1 to 40%.

6. The press-coated orally-disintegrating tablet of claim 1 wherein the inner core comprises an active ingredient.

\* \* \* \* \*